(12) United States Patent
Ogawa et al.

(10) Patent No.: US 9,627,173 B2
(45) Date of Patent: Apr. 18, 2017

(54) STAGE DEVICE AND CHARGED PARTICLE BEAM APPARATUS USING THE STAGE DEVICE

(71) Applicant: Hitachi High-Technologies Corporation, Minato-ku, Tokyo (JP)

(72) Inventors: Hironori Ogawa, Tokyo (JP); Masaki Mizuochi, Tokyo (JP); Shuichi Nakagawa, Tokyo (JP); Tsukasa Sugawara, Tokyo (JP)

(73) Assignee: Hitachi High-Technologies Corporation, Tokyo (JP)

( * ) Notice: Subject to any disclaimer, the term of this patent is extended or adjusted under 35 U.S.C. 154(b) by 58 days.

(21) Appl. No.: 14/626,041

(22) Filed: Feb. 19, 2015

(65) Prior Publication Data

US 2015/0248991 A1    Sep. 3, 2015

(30) Foreign Application Priority Data

Feb. 28, 2014  (JP) ................................. 2014-037689

(51) Int. Cl.
*H01J 37/20* (2006.01)
*G01B 9/02* (2006.01)
*G01N 23/22* (2006.01)
*G01B 15/00* (2006.01)

(52) U.S. Cl.
CPC .......... *H01J 37/20* (2013.01); *G01B 9/02021* (2013.01); *G01B 9/02027* (2013.01); *G01N 23/2204* (2013.01); *G01B 15/00* (2013.01); *H01J 2237/20292* (2013.01); *H01J 2237/2817* (2013.01)

(58) Field of Classification Search
CPC .......... H01J 37/20; H01J 37/26; H01J 37/261; H01J 37/28; H01J 37/3171; H01J 2237/20292; H01J 2237/2817; G01B 9/02021; G01B 9/02027; G01B 15/00
See application file for complete search history.

(56) References Cited

U.S. PATENT DOCUMENTS

| | | | | |
|---|---|---|---|---|
| 6,486,941 | B1 * | 11/2002 | Hazelton | G03F 7/70716 |
| | | | | 355/53 |
| 6,630,681 | B1 * | 10/2003 | Kojima | B82Y 10/00 |
| | | | | 250/282 |
| 2002/0149136 | A1 * | 10/2002 | Baird | B23K 26/083 |
| | | | | 264/400 |
| 2003/0234939 | A1 * | 12/2003 | Kurosawa | G03F 7/70775 |
| | | | | 356/500 |

(Continued)

FOREIGN PATENT DOCUMENTS

JP        2556361 B2    11/1996

*Primary Examiner* — David E Smith
(74) *Attorney, Agent, or Firm* — Crowell & Moring LLP (57) ABSTRACT

To attain the above object, in the present invention, proposed are a stage apparatus including a sample stage that mounts a sample, a first position detection device that detects a position of the sample stage, a second position detection device that detects a position of the sample stage when the sample stage is positioned in a part of a stage movement range that the first position detection device is capable of detecting, and a control device that adjusts an offset amount of the first position detection device on the basis of a position detection result obtained by the second position detection device, and a charged particle beam apparatus using the stage apparatus.

22 Claims, 8 Drawing Sheets

(56) References Cited

U.S. PATENT DOCUMENTS

| | | | |
|---|---|---|---|
| 2004/0041101 A1* | 3/2004 | Akutsu | H01J 37/3045 250/491.1 |
| 2004/0114218 A1* | 6/2004 | Karlsson | G02B 21/26 359/368 |
| 2008/0013099 A1* | 1/2008 | Akimoto | G03F 7/70733 356/509 |
| 2010/0157271 A1* | 6/2010 | Van Weert | G03F 7/70341 355/71 |
| 2011/0053061 A1* | 3/2011 | Shibazaki | G03F 7/70725 430/30 |

* cited by examiner

STAGE DEVICE AND CHARGED PARTICLE BEAM APPARATUS USING THE STAGE DEVICE

BACKGROUND OF THE INVENTION

The present invention relates to a stage apparatus and a charged particle beam apparatus, and particularly to a stage apparatus that specifies a stage position by irradiating beams on a reflecting mirror and a charged particle beam apparatus that includes the stage apparatus.

Along with miniaturization of semiconductor devices, high accuracy compatible with the miniaturization is required for not only manufacturing equipment but also inspection equipment and evaluation equipment. To evaluate patterns formed on a semiconductor wafer or inspect defects in a formed wafer, a scanning electron microscope (hereinafter, referred to as an SEM) is normally used and particularly, to evaluate a shape size of patterns, a critical dimension SEM is used.

The critical dimension SEM is a device that irradiates electron beams on a wafer, performs image processing on obtained secondary electron signals, determine an edge of a pattern from a change in light and darkness, and calculates sizes, etc. To observe and inspect the entire area of a wafer, on the critical dimension SEM, provided is an X-Y stage that is capable of positioning a desired portion of the wafer as an irradiation position of beams. In the X-Y stage, for example, a method in which the X-Y stage is driven by a rotation motor and ball screws, or a method in which the X-Y stage is driven by a linear motor is used. In addition, an X-Y stage may be used in which a rotary motion and the like are performed not only on an X-Y plane and but also on a Z axis or around the Z axis.

In the X-Y stage, for accurately performing positioning of wafers, it is necessary to perform detection of a stage position with high accuracy. For this purpose, known is a method in which a laser interferometer and a reflecting mirror are used.

A laser interferometer is capable of irradiating laser light on a reflecting mirror and detecting a stage position with a resolution of several tens of picometer order due to interference with reflected waves. Further, since measurement can be performed at the same height as that of a wafer, an Abbe error is minimized; therefore, a laser interferometer is widely used for position measurement in lots of precision stages including the critical dimension SEM.

In the critical dimension SEM, to cope with enlargement of wafers or diversification of wafer inspection means, a stroke of the X-Y stage is required to be increased. When wafers are observed by the wafer inspection means (for example, an optical microscope and the like) other than an SEM, a stroke of the X-Y stage is further required to be increased.

When the stroke of the X-Y stage is increased, elongation of the reflecting mirror is required with an increase in the stroke for reflecting laser light over the entire stroke. In this case, it is difficult to assure flatness of a plane of the reflecting mirror, and at the same time an increase in vibrations due to the elongation results in degradation of the measurement accuracy. Further, for assuring a motion space of the elongated reflecting mirror, a sampling chamber itself is required to be grown in size, and as a result it causes an increase in cost of manufacture and transportation and an enlargement of an installation area.

In JP2556361, disclosed is a technology of switching to a stage-positioning system using a length measurement system (for example, a linear scale) in which a size of a mirror is minimized and a mirror is not used other than a positioning range by laser light.

SUMMARY OF THE INVENTION

When a technology disclosed in JP2556361 is applied to a charged particle beam apparatus such as the critical dimension SEM, the reflecting mirror can be shortened by switching a laser interferometer and a linear scale. However, the linear scale and the laser interferometer are attached to different positions at least in the height direction, and therefore an Abbe error occurs. That is, there is the possibility that correspondence of the laser interferometer with the linear scale is not uniquely determined depending on an attitude angle (pitching or rolling) of the sample stage, and as a result positioning accuracy after the switching cannot be sufficiently assured.

Hereinafter, provided are the sample stage in which even if the sample stage is out of a position-detectable region by a position detection device such as a laser interferometer, when the sample stage returns to the position-detectable region, a position can be detected with high accuracy by the position detection device as an object, and the charged particle beam apparatus using the sample stage.

According to an embodiment for attaining the above object, hereinafter, provided are a stage apparatus including a sample stage that mounts a sample, a first position detection device that detects a position of the sample stage, a second position detection device that detects a position of the sample stage when the sample stage is positioned in a part of a stage movement range that the first position detection device is capable of detecting, and a control device that adjusts an offset amount of the first position detection device on the basis of a position detection result obtained by the second position detection device, and a charged particle beam apparatus using the stage apparatus.

According to the above configuration, even if the sample stage is out of a position-detectable region by a position detection device such as a laser interferometer, when the sample stage returns to the position-detectable region, a position can be detected with high accuracy by the position detection device, and therefore miniaturization of a reflecting mirror is compatible with an accurate position detection.

DESCRIPTION OF THE EMBODIMENTS

The present embodiment described below relates mainly to a stage apparatus in which a laser interferometer and a linear scale can be switched and a stage position can be measured with high accuracy, and a charged particle beam apparatus.

In the present embodiment described below, proposed are mainly a stage apparatus including a base, a sample stage that is capable of being moved to the base, a reflecting mirror that is provided on the sample stage, a laser interferometer that measures a position of the sample stage by irradiating laser light on the reflecting mirror, a control device that controls a position of the sample stage, an absolute position detection device that measures an absolute amount of a distance between the base and the sample stage, and a third position detection device that is different from the laser interferometer and the absolute position detection device, wherein the control device positions the sample stage in a position that the laser interferometer and the absolute position detection device are capable of detecting and changes an offset amount of the laser interferometer by position information measured by the absolute position detection device, and a charged particle beam apparatus including the stage apparatus.

According to the above configuration, the stage apparatus can be realized in which the laser interferometer and the linear scale are used at the same time and in which both of them can be switched with high accuracy and an accurate stage position can be measured.

The present embodiment described below relates to the charged particle beam apparatus such as a critical dimension SEM, and the accurate stage apparatus that is applicable thereto. Hereinafter, the present embodiment will be described with reference to the accompanying drawings.

First Embodiment

Figure 1:
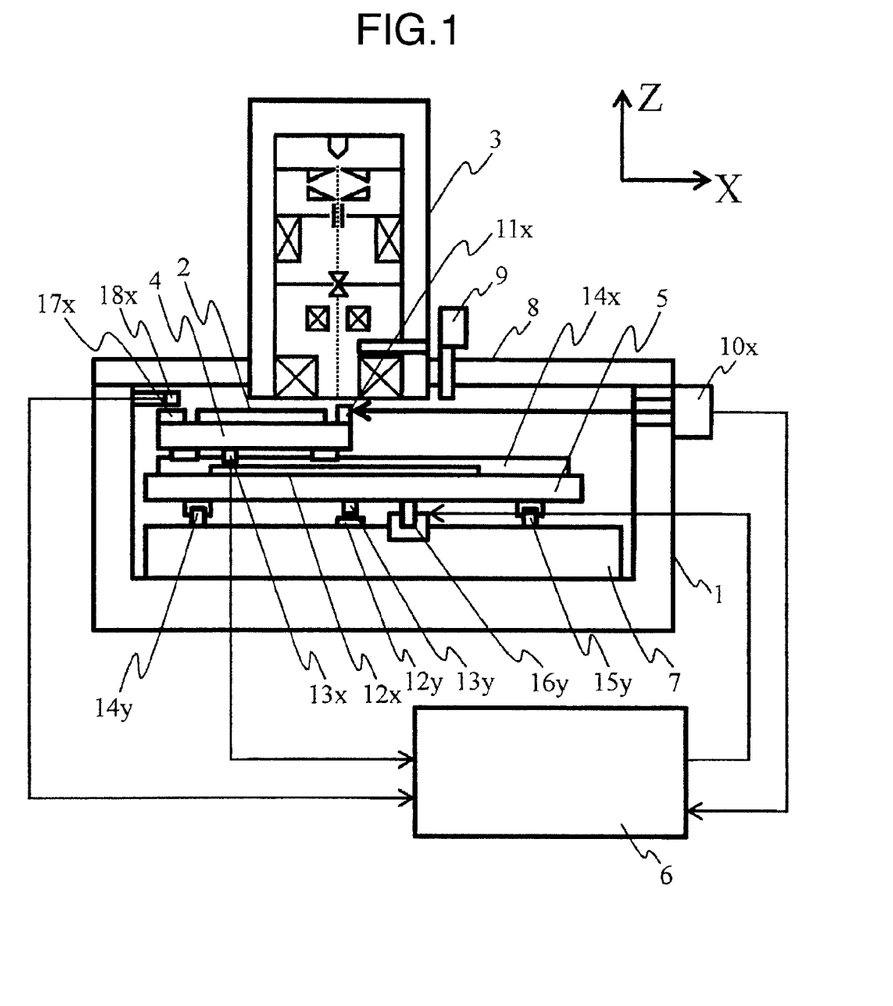
FIG. 1 is a cross-sectional configuration diagram illustrating a charged particle beam apparatus (first embodiment)

FIG. 1 is a cross-sectional configuration diagram illustrating the charged particle beam apparatus according to the present embodiment. In FIG. 1, a Y table 5 that is capable of being freely moved in a Y direction (in the depth direction of the sheet) through two Y linear guides 14y and 15y is arranged on a base 7 fixed on a sample chamber 1. At the same time, a Y linear motor 16y is arranged so as to relatively generate thrust in the Y direction between the base 7 and the Y table 5. On the Y table 5, an X table 4 that is capable of being freely moved in the X direction through two X linear guides 14x and 15x (not illustrated) is arranged. At the same time, an X linear motor 16x (not illustrated) is arranged so as to generate thrust in the X direction between the X table 4 and the Y table 5. The process permits the X table 4 to be freely moved in the X and Y directions to the base 7 and the sample chamber 1.

On the X table 4, a wafer 2 is arranged. A wafer holding mechanism including a holding power such as a mechanical restriction force or an electrostatic force is used for the arrangement of the wafer 2. On the sample chamber 1, a top board 8 and a column 3 are arranged. In the column 3, included is an electronic optical system that generates a secondary electron image by using electron beams. Further, on the top board 8, an optical microscope 9 that observes the wafer 2 at a low magnification is arranged.

On the base 7, a Y linear scale 12y is arranged in the Y direction, and a Y linear scale detector 13y is arranged on the Y table 5 so as to face the Y linear scale 12y. The Y linear scales (12y and 13y) (third position detection device in the Y direction) measure an amount of relative displacement in the Y direction (hereinafter, referred to as a Y scale value) of the Y table 5 and the base 7. Similarly, on the Y table 5, an X linear scale 12x is arranged, and an X linear scale detector 13x is arranged on the X table 4 so as to face the X linear scale 12x. The X linear scales (12x and 13x) (third position detection device in the X direction) measure an amount of relative displacement in the X direction (hereinafter, referred to as an X scale value) of the X table 4 and the Y table 5. Through the above configuration, the amount of relative displacement in each of the X and Y directions of the X table 4 and the base 7 can be measured.

On the X table 4, an X mirror 11x is arranged, and on a side face of the sample chamber 1, an X laser interferometer 10x is arranged (first position detection device in the X direction). The X laser interferometer 10x irradiates laser light on the X mirror 11x and measures the amount of relative displacement (hereinafter, referred to as an X laser value) in the X direction of the sample chamber 1 and the X table 4 by using reflected light thereof. Here, the X mirror 11x has a mirror surface on a Y-Z plane and has a long rod shape in the Y direction. Further, the X mirror 11x is capable of reflecting laser light also when the Y table 5 is moved in the Y direction. In addition, the X mirror 11x is arranged so that the laser light is generally matched with a top face (measuring plane) of the wafer 2 in a height in the Z direction. With regard to the Y direction, similarly, the amount of relative displacement (hereinafter, referred to as a Y laser value) in the Y direction of the sample chamber 1 and the X table 4 can be measured by a Y laser interferometer 10y (first position detection device in the Y direction; not illustrated) and a Y mirror 11y (not illustrated).

Here, both of the X laser value and the X scale value indicate the amount of relative displacement in the X direction of the X table 4 to the sample chamber 1. However, both of them are not accurately matched with each other due to an Abbe error. That is, a measuring position of the X laser value and the X scale value has an offset in the Z direction, and therefore the Abbe error occurs when an attitude angle of the X table 4 changes due to a movement or vibrations of the table. Similarly, also in the Y laser value and the Y scale value, the Abbe error occurs.

In a control device 6, an operation processing unit, an amplifier for driving motor, and the like are included. The control device 6 receives laser values and scale values in the X and Y directions as inputs, and controls a driving current of the linear motors. Thereby, the control device 6 drives the stage in the X and Y directions and performs positioning in a desired position. Here, in a method for controlling the linear motor, a PID control or the like can be used.

Through the above configuration, the wafer 2 is moved to the sample chamber 1 on the X and Y plane, and a secondary electron image can be generated by the column 3.

On the X table 4, an X absolute scale 17x is arranged, and an X absolute scale detector 18x is arranged in the sample chamber 1 (second position detection device in the X direction). Here, the X absolute scale 17x is arranged so that a measuring plane of the wafer 2 is generally matched with laser light from the X laser interferometer 10x in the height in the Z direction. Also with regard to the Y direction, a Y absolute scale 17y and a Y absolute scale detector 18y (second position detection device in the Y direction; both of them are not illustrated) are similarly arranged. A detailed arrangement and a usage method of the absolute scales will be described later. In addition, in the present embodiment, the absolute scale detectors (18x and 18y) are arranged in the sample chamber 1, and further can be arranged in the base, the top board, the column, or the like.

In the present embodiment, the linear guides are used as a guiding mechanism; further, another guiding mechanism (for example, a fluid dynamic bearing, a magnetic bearing, or the like) can be used. Further, the linear motor is used as the drive mechanism; for example, an actuator capable of being used in vacuum, such as a ball screw or a piezoelectric actuator can be used.

Figure 2:
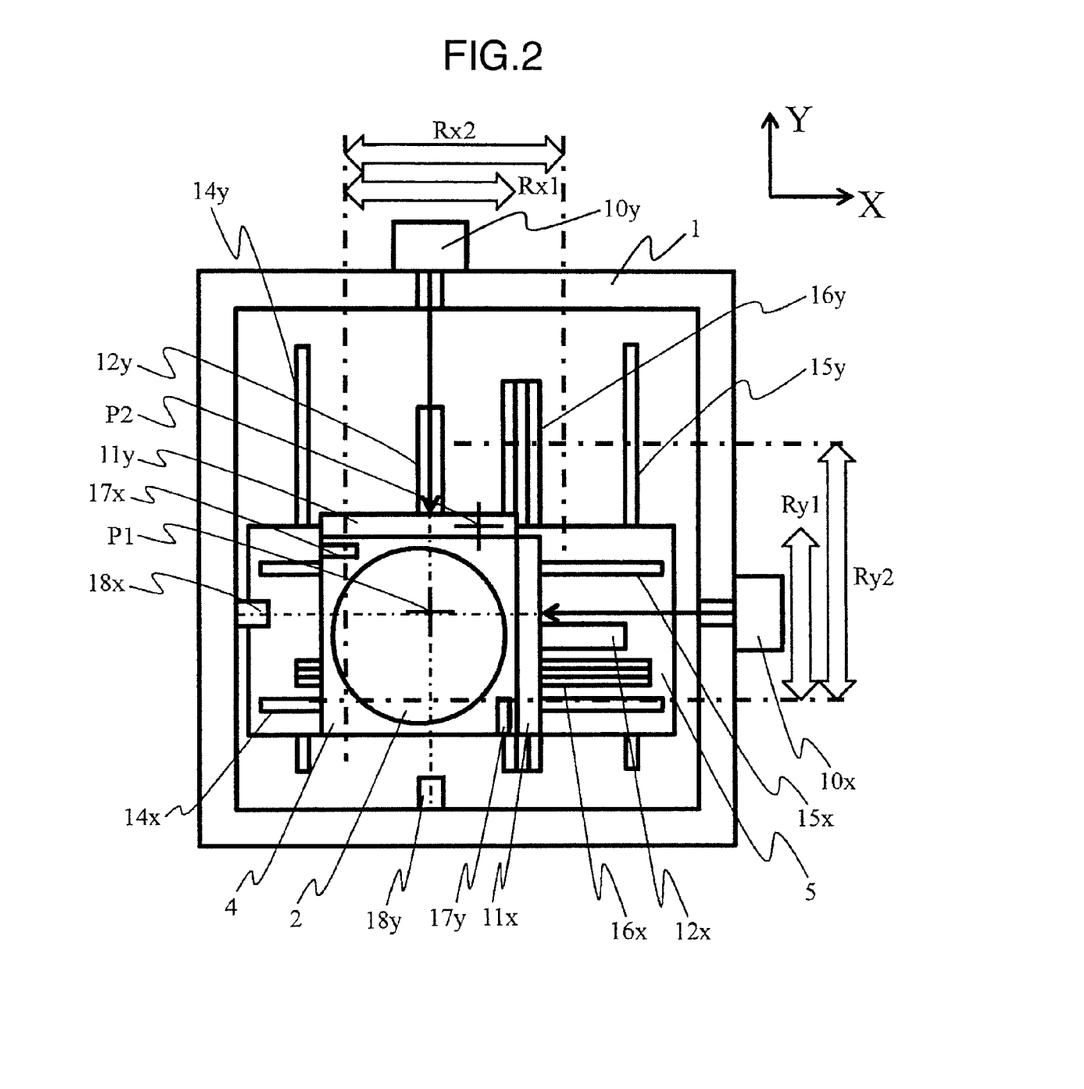
FIG. 2 is a top configuration diagram illustrating the charged particle beam apparatus (laser visible-state) (first embodiment)

FIG. 2 is a top configuration diagram illustrating the charged particle beam apparatus according to the present embodiment, and illustrates a table position arrangement in a laser visible-state.

Laser light from the laser interferometers 10x and 10y is irradiated on the mirrors 11x and 11y, and X and Y coordinates of the wafer 2 can be measured by both of the scale values and the laser values.

A position P1 of FIG. 2 illustrates an intersection point of the laser light irradiated from the laser interferometers 10x and 10y, and the column 3 is arranged so that a center (position on which an electron beam to acquire a secondary electron image is irradiated) of the column 3 is matched with the position P1. Through the process, position information about a measuring point (electron beam irradiation position) to an attitude change (yawing) around the Z axis of the wafer 2 can be measured without the Abbe error by using the laser values. A stroke of the table in each of the X and Y directions necessary to observe the whole plane of the wafer 2 through the column 3 is in the range of Rx1 and Ry1 of FIG. 2.

A position P2 is an observable position through the optical microscope 9. Because of restrictions of a size of the electronic optical system in the column 3, normally, it is difficult to arrange the position P2 in the same position as the position P1, and both of them have an offset. A stroke of the table in each of the X and Y directions necessary to observe the whole plane of the wafer 2 through the optical microscope 9 is in the range of Rx2 and Ry2 of FIG. 2. In the present embodiment, the optical microscope is used as a detection means other than an SEM. Further, also in the case in which other detection means or sensors for observing or sensing the wafer 2 are used, the present configuration is effective.

Here, during the observation by the SEM, it is necessary to accurately detect position information about the wafer 2 (without the Abbe error), and therefore it is essential to perform positioning of the stage by using the laser values. On the other hand, the optical microscope 9 is used at the low magnification as compared to the SEM, and therefore even if the stage is positioned not by using accurate laser values but by using the scale values, sufficient image accuracy can be assured. That is, with regard to the X direction, for example, the X laser values are preferably used in the range of the Rx1, and the X scale values are used in the range other than Rx1 of Rx2. Through the above, in the present embodiment, a length of the Y mirror 11y is determined so as to cover the range of the Rx1 and a length of the X mirror 11x is determined so as to cover the range of the Ry1; thereby, an essential mirror length is obtained.

In FIG. 2, since the laser values and the scale values are obtained together, driving current of the linear motors (16x and 16y) is preferably determined by both of them in the control device 6. Further, the absolute scales (17x and 17y) and the absolute scale detectors (18x and 18y) exist separately from each other, and therefore position detection cannot be performed.

Figure 3:
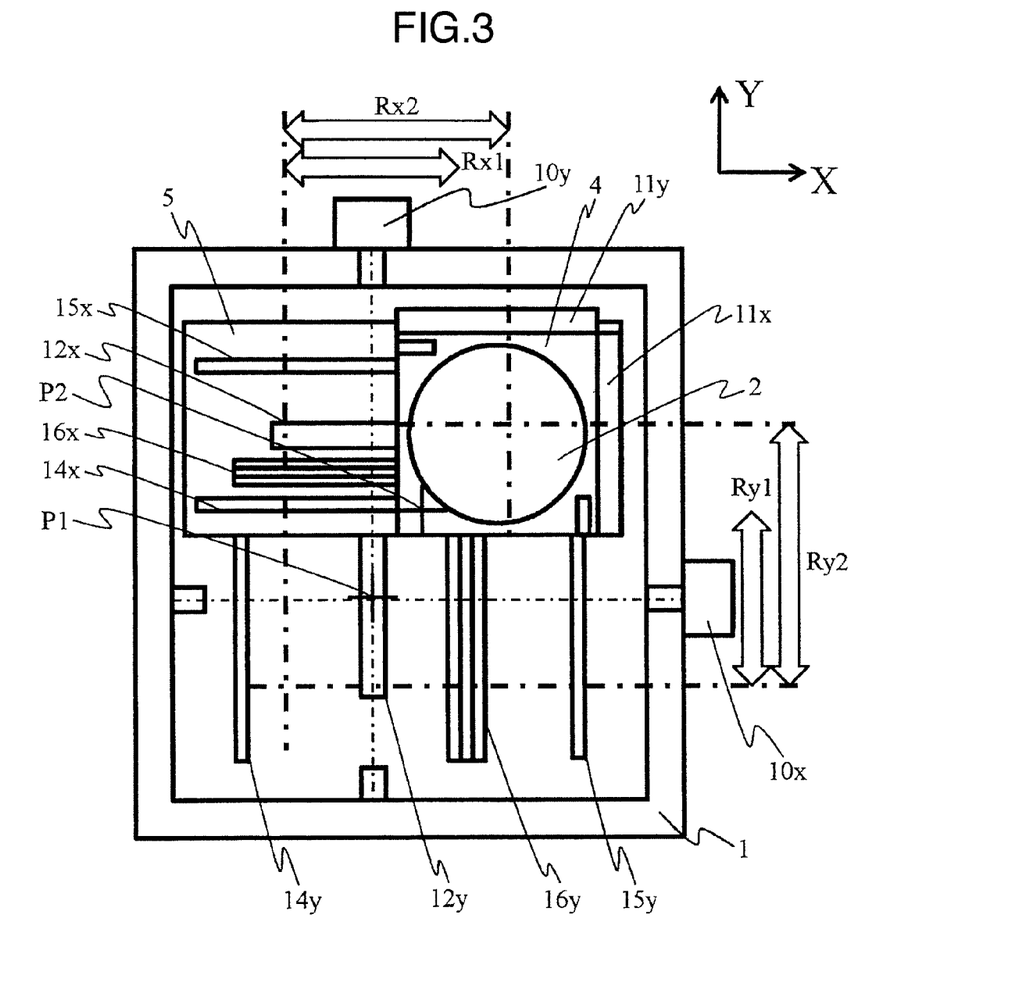
FIG. 3 is a top configuration diagram illustrating the charged particle beam apparatus (laser invisible-state) (first embodiment)

FIG. 3 is a top configuration diagram illustrating the charged particle beam apparatus according to the present embodiment, and illustrates a table position arrangement in a laser invisible-state. Laser light from the laser interferometers 10x and 10y is not irradiated on the mirrors 11x and 11y, and therefore the X and Y coordinates of the wafer 2 can be measured by only the scale values. Accordingly, the control device 6 controls driving current of the linear motors (16x and 16y) by using only the scale values. Further, the absolute scales (17x and 17y) and the absolute scale detectors (18x and 18y) exist separately from each other, and therefore position detection cannot be performed.

Figure 4:
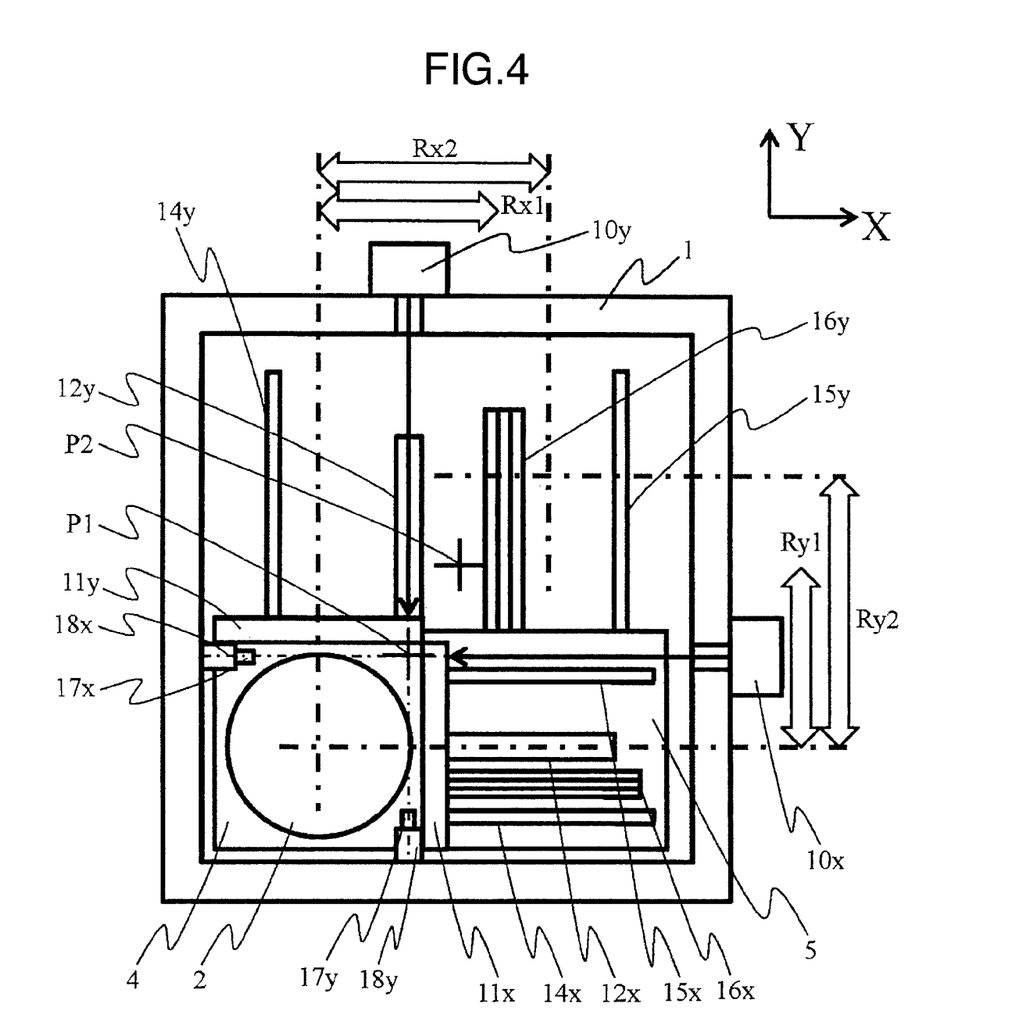
FIG. 4 is a top configuration diagram illustrating the charged particle beam apparatus (switching state) (first embodiment)

FIG. 4 is a top configuration diagram illustrating the charged particle beam apparatus according to the present embodiment, and illustrates a table position arrangement in a switching state. The laser light from the laser interferometers 10x and 10y is irradiated on the mirrors 11x and 11y, and the X and Y coordinates of the wafer 2 can be measured by both of the scale values and the laser values. Further, the X absolute scale 17x faces the X absolute scale detector 18x, and the Y absolute scale 17y faces the Y absolute scale detector 18y. Therefore, a physical position (hereinafter, referred to as an absolute scale value) in the X and Y directions of the X table 4 to the sample chamber 1 can be accurately measured.

Further, the X table 4 is arranged so that a direction of the laser light and a measuring direction of the absolute scales are matched with each other, and further is arranged so that a measuring point of the wafer 2 falls on a line thereof. Therefore, it is preferable that as illustrated in FIG. 4, the absolute scales are arranged on the opposite side of the reflecting mirrors 11 on the X table 4. Through the arrangement as described above, the Abbe error does not occur between the laser values and position information about the absolute scales as well as a measuring point of the wafer 2, and therefore an accurate position measurement can be performed. On the other hand, since the laser interferometer measures the amount of relative displacement, a physical distance can be calculated by determining a reference position. However, the above cannot be realized by only the laser interferometer itself. Further, even if the absolute scales are used as the linear scales (12 and 13), an error that occurs by an influence of the Abbe error cannot be removed.

As described above, in a stage position (hereinafter, referred to as a switching position) illustrated in FIG. 4, when the reference position of the laser value can be accurately set (offset adjusted) by the absolute scale value, a position measurement can be performed subsequently with high accuracy in the effective range of laser light.

Figure 5:
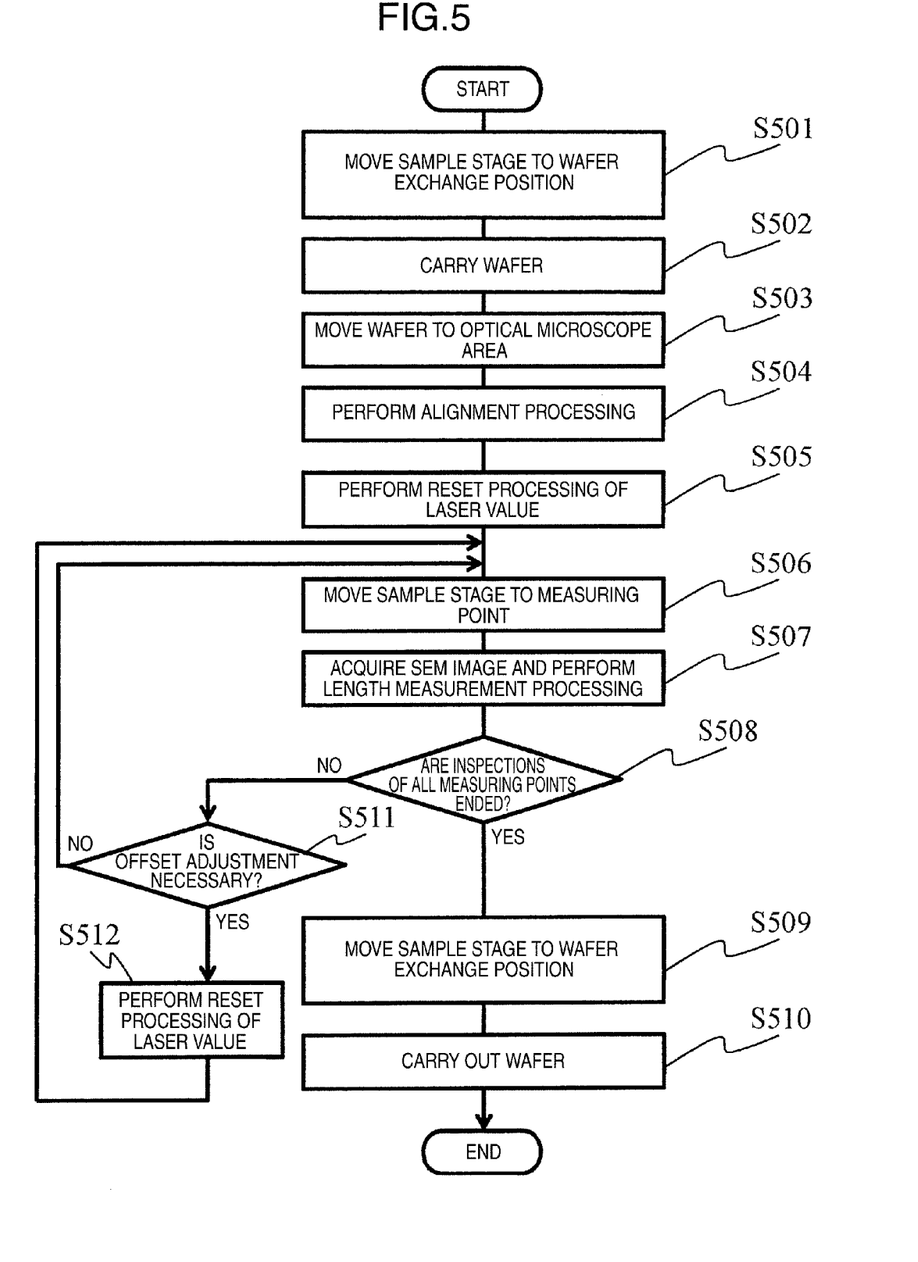
FIG. 5 is a flowchart illustrating an inspection process of the charged particle beam apparatus (first embodiment)

FIG. 5 is a flowchart illustrating an inspection process of the charged particle beam apparatus according to the present embodiment. At process S501, the stage is moved to a wafer exchange position. In the present embodiment, the wafer exchange position is not illustrated; however, it can be arbitrarily set in a movable range of the stage regardless of the visible-state and/or invisible-state of laser light.

At process S502, by using a carrying robot or the like, the wafer 2 is arranged in a wafer supporting member on the X table 4 in the sample chamber 1, and at the same time is held by the wafer holding mechanism. At process S503, the wafer 2 is moved in the visible range of the optical microscope 9. Here, the stage control is performed by only the scale values.

At process S504, alignment processing is performed by the optical microscope 9. Here, in the alignment processing, a movement of the stage and imaging by the optical microscope 9 are performed more than once, and corrections of a mounting position and an angle of the wafer 2 are performed on the basis of the obtained images. At process S505, reset processing as described later of the laser values is performed and switching is performed from control of using only the scale values to control of using the laser values.

At process S506, the stage is moved to a previously-registered measuring point on the wafer 2. At process S507, SEM images are obtained and length measurement processing is performed. Here, addressing processing for accurately detecting positions of measuring points, focusing processing, high magnification image acquisition processing, and the like are performed by the SEM images.

At process S508, it is determined whether all of the previously-registered measuring points are inspected. At process S509, the stage is moved to the wafer exchange position. At process S510, the holding mechanism is released, and at the same time the wafer 2 is carried out of the sample chamber 1 by using the carrying robot or the like. At process S511, it is determined whether the offset adjustment is necessary. Here, in the determination whether the offset adjustment is necessary, a method is effective in which the offset adjustment is determined to be necessary in the case in which a certain period of time has elapsed by an elapsed time, or a method is effective in which the offset adjustment is determined to be necessary in the case in which after the offset adjustment is performed previous time, a temperature change is measured by a thermometer and the temperature is more than a threshold. At process S512, the reset processing of the laser values is performed in the same manner as in the process S505, and the offset amount is adjusted.

Figure 6:
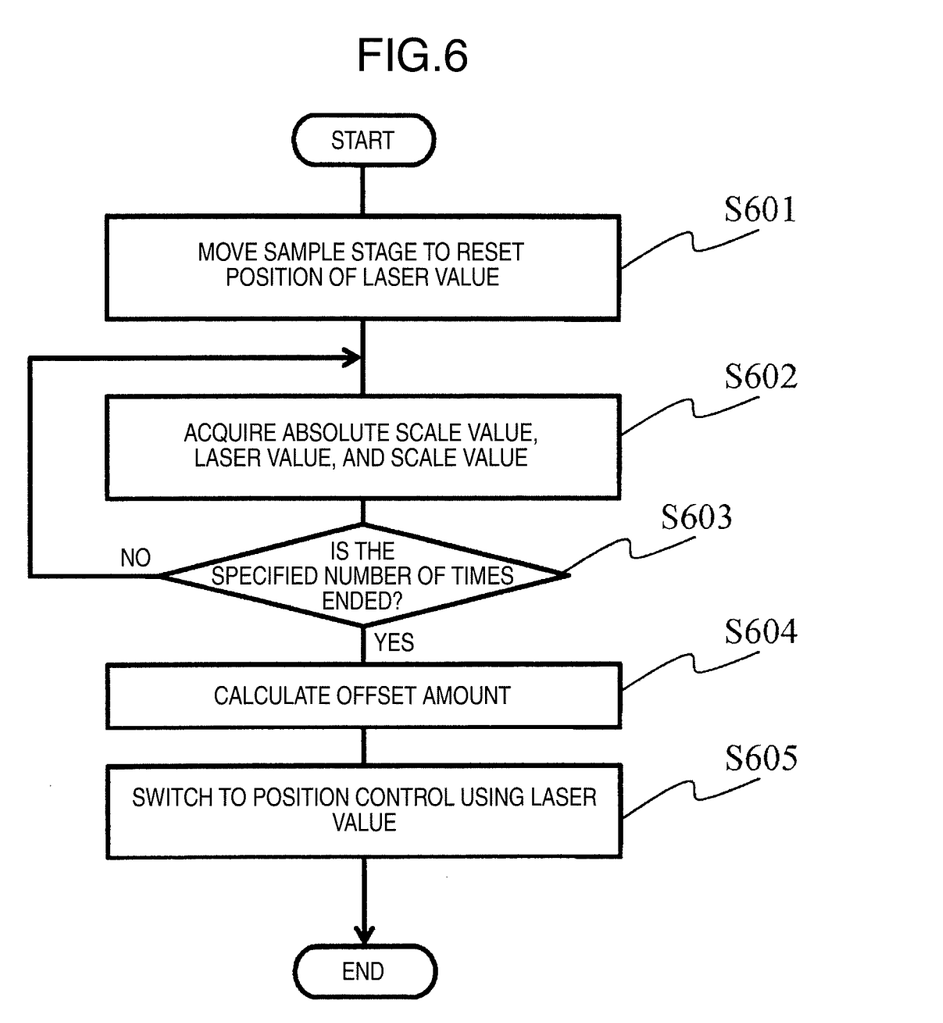
FIG. 6 is a flowchart illustrating reset processing of a laser value of the charged particle beam apparatus (first embodiment)

FIG. 6 is a flowchart illustrating the reset processing of the laser values according to the present embodiment. For purposes of illustration, equations represent only the X direction and the laser values can be calculated also in the Y direction just the same.

At process S601, the stage is moved to a predetermined switching position. At this time, the control device 6 performs control by using only the scale values. At process S602, laser values Lx, scale values Sx, and absolute scale values Ax in the X direction are obtained and added to integrated values SLx, SSx, and SAx.

At process S603, it is determined whether the specified number of times N previously determined is ended. At process S604, an average laser value ALx, an average scale value ASx, and an average absolute scale value AAx of N times are first calculated by equations 1, 2, and 3. Here, a noise component is removed by increasing the average number of times N and the measurement can be performed to an accuracy of nanometer order. However, when the average number of times N is extremely increased, the time is required during the measurement, and therefore it is preferable that the measurement is generally performed to an accuracy of about several tens of millisecond order to one second order.

$$ALx=SLx/N \quad \text{(Equation 1)}$$

$$ASx=SSx/N \quad \text{(Equation 2)}$$

$$AAx=SAx/N \quad \text{(Equation 3)}$$

Next, the offset amount of the laser values and the scale values is calculated by equations 4 and 5.

$$OfsLx=ALx-AAx+Px \quad \text{(Equation 4)}$$

$$OfsSx=ASx-AAx+Px \quad \text{(Equation 5)}$$

Here, a symbol OfsLx denotes the offset amount of the X laser value, a symbol OfsSx denotes the offset amount of the X scale value, a symbol Px denotes a coordinate of the switching position, and the offset amount is calculated so that an X coordinate of the switching position is equal to Px.

At process S605, switching to the position control of using the laser values is performed by the obtained offset amount. By using the offset amount calculated by the equations 4 and 5, position information PosLx and PosLy used in the control is calculated by equations 6 and 7.

$$PosLx=Lx-OfsLx \quad \text{(Equation 6)}$$

$$PosSx=Sx-OfsSx \quad \text{(Equation 7)}$$

In addition, the switching procedure illustrated in FIG. 6 can be performed not only during the inspection process illustrated in FIG. 5 but also at arbitrary timing. For example, when a pattern observation is performed while comparing images of the optical microscope 9 and the SEM images, the switching process can be performed before the SEM images are obtained.

According to the stage apparatus and charged particle beam apparatus configured as described above, the laser interferometers and the linear scales are used at the same time, and thereby sizes of the mirror 11 and the sample chamber 1 can be minimized. At the same time, the laser values and the scale values can be switched with high accuracy and used. Further, a positioning error of the wafer 2 caused by thermal expansion and the like can be suppressed.

In the present embodiment, the absolute scales are used in order to determine a physical position relationship between the sample chamber 1 and the X table 4. Similarly, a sensor capable of measuring a physical position, such as a sensor using electrostatic capacity, laser, supersonic wave, magnetism, or the like can be used. Further, a method is also effective in which a new sensor is not used but the physical position relationship is determined by the SEM images or the optical microscope images. In addition, the above sensors and means are used in plurality at the same time, and thereby an improvement in the accuracy can be further expected.

As described above, according to the present embodiment, when the sample stage is positioned in a part of a stage movement range that the position detection device is capable of detecting by the laser interferometer 10, the position detection is performed by an absolute position detector that is capable of detecting a position of the sample stage. Through the process, since the position detection accuracy of the laser interferometer 10 is compensated, even if the stage is positioned out of the position detection range by the laser interferometer 10, high position detection accuracy can be maintained. As a result, while a length of the reflecting mirror 11 necessary for the laser interferometer 10 is shortened, high-accuracy positioning can be performed.

Second Embodiment

Figure 7:
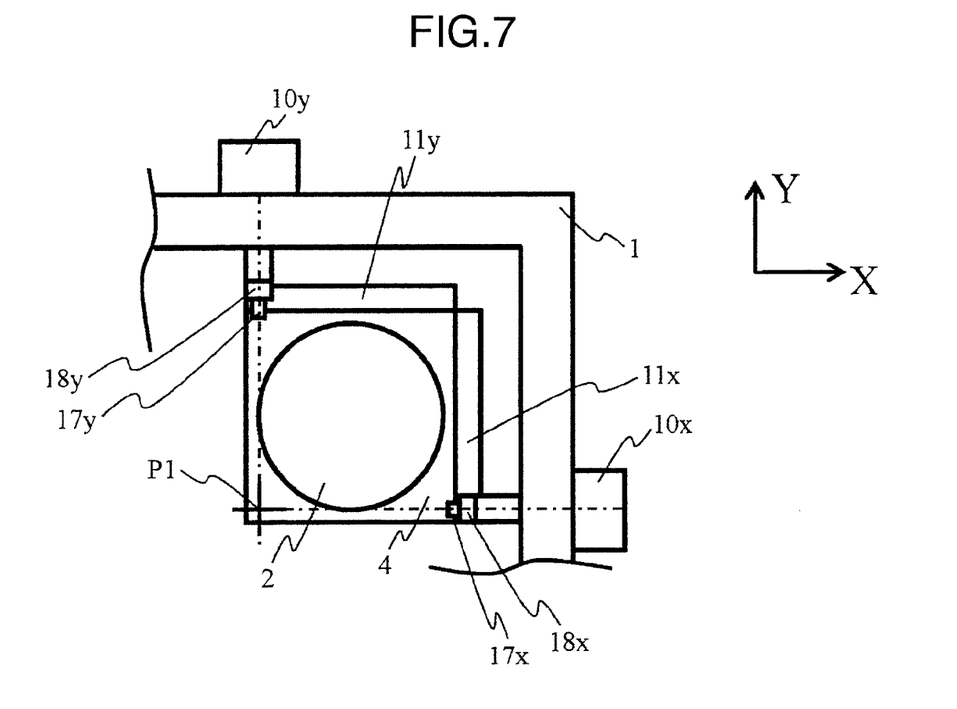
FIG. 7 is a top configuration diagram illustrating the charged particle beam apparatus (second embodiment)
Figure 8:
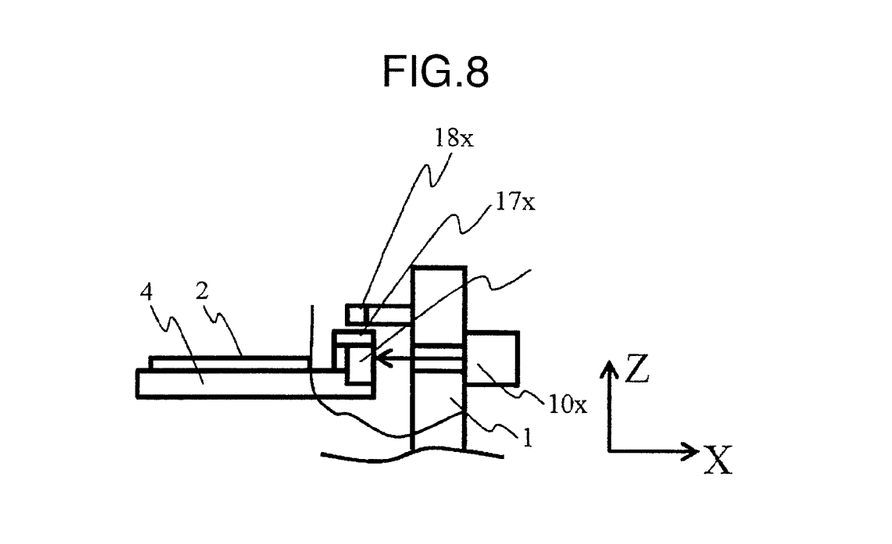
FIG. 8 is a side configuration diagram illustrating the charged particle beam apparatus (second embodiment)

FIG. 7 is a top configuration diagram illustrating the charged particle beam apparatus according to the present embodiment, and FIG. 8 is a side configuration diagram illustrating the charged particle beam apparatus according to the present embodiment. In FIGS. 7 and 8, members indicated by the same numbers as those of FIGS. 1 to 4 each have the same configuration and function, and therefore descriptions will be omitted.

In FIGS. 7 and 8, the X absolute scale 17x is arranged at the end of the X mirror 11x side on the X table 4, and the X absolute scale detector 18x is arranged near the X laser interferometer 10x. Similarly, the Y laser interferometer 10y and the Y absolute scale 17y are arranged on the Y mirror 11y side, and the Y absolute scale detector 18y is arranged near the Y laser interferometer 10y. In the case of the arrangement as described above, a difference occurs slightly in the height in the Z direction between the laser light and the absolute scale, and therefore the Abbe error occurs slightly. However, as compared to the scale values, an error is suppressed to the extremely small Abbe error, and therefore an effect of switching the laser values and the scale values with high accuracy can be expected also in the configuration according to the present embodiment.

Third Embodiment

Figure 9:
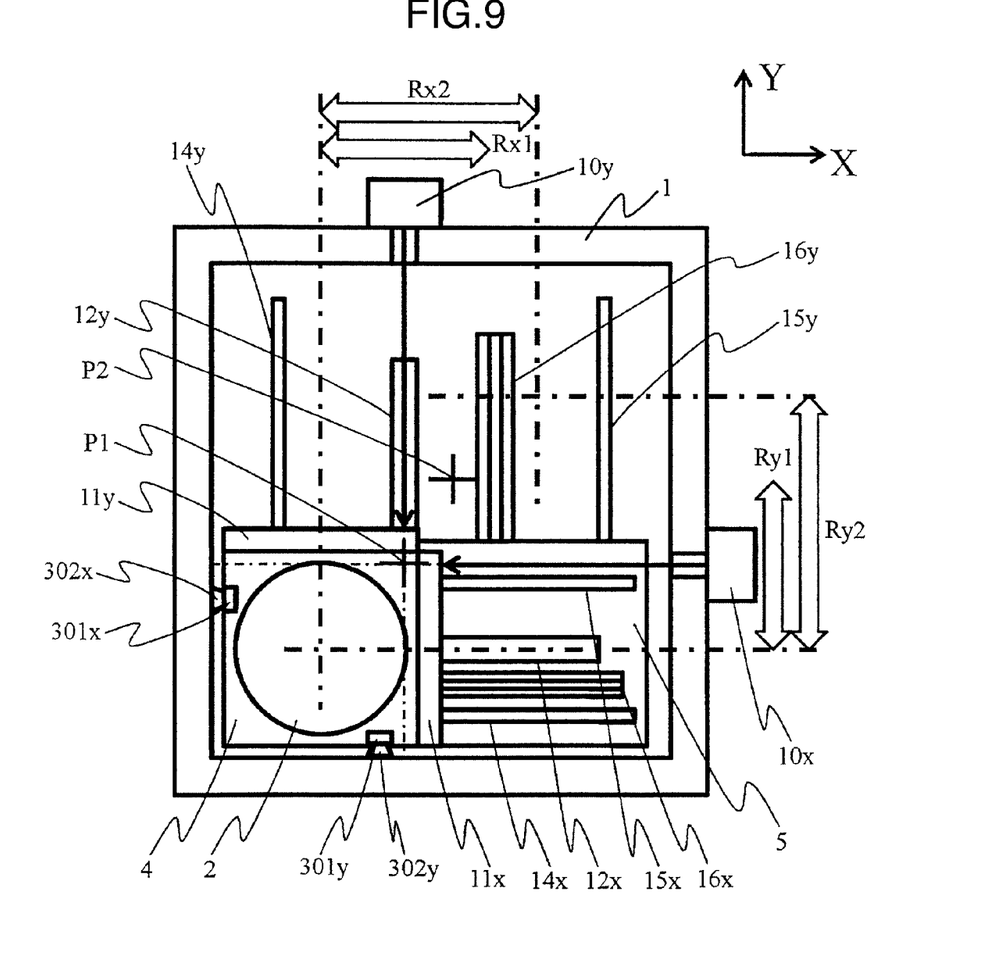
FIG. 9 is a top configuration diagram illustrating the charged particle beam apparatus (switching state) (third embodiment).

FIG. 9 is a top configuration diagram illustrating the charged particle beam apparatus according to the present embodiment, and illustrates a table position arrangement in the switching state. In FIG. 9, members indicated by the same numbers as those of FIG. 2 each have the same configuration and function, and therefore descriptions will be omitted.

In FIG. 9, an X pressing member 301x is arranged near an end face in the X direction on the X table 4, and an X pressed member 302x is arranged on an inner wall of the sample chamber 1 in a position facing the X pressing member 301x. Similarly, a Y pressing member 301y is arranged on the X table 4, and a Y pressed member 302y is arranged on an inner wall of the sample chamber 1 in a position facing the Y pressing member 301y.

When the offset adjustment of the scale values and the laser values is performed, the pressing members 301 are pressed against the pressed members 302 by the linear motors (16x and 16y) and the offset amount of the laser values is calculated in a state in which constant thrust is generated.

Through the process, a new sensor is not used but an adjustment of the offset amount can be performed with high accuracy by restricting a physical position relationship between the sample chamber 1 and the X table 4.

In addition, a member having high elasticity (for example, spring-shaped metal, rubber, or resin materials) is effectively used for the pressing members 301 and the pressed members 302.

Further, in FIG. 9, the pressing member and the pressed member are each arranged by one in the X and Y directions. Further, a method for arranging a plurality of the pressing members and the pressed members can be used, or a method for pressing a continuous member as a surface contact can be used. Further, the pressing members 301 are not used but, for example, a method for pressing a side face of the X stage can be used.

The invention claimed is:

1. A stage apparatus comprising:
a sample stage that mounts a sample;
a first position detection device that detects a position of the sample stage;
a second position detection device that detects a position of the sample stage when the sample stage is positioned in a part of a stage movement range that the first position detection device is capable of detecting; and
a control device that adjusts an Abbe error offset amount of the first position detection device on a basis of a position detection result obtained by the second position detection device.

2. The stage apparatus according to claim 1, wherein the second position detection device is an absolute position detection device that measures an absolute amount of a distance between the sample stage and a base on which the sample stage is arranged.

3. The stage apparatus according to claim 2, wherein the absolute position detection device is arranged on the sample stage.

4. The stage apparatus according to claim 2, wherein the first position detection device includes a reflecting mirror that is installed on the sample stage and a laser interferometer that detects a position of the sample stage by irradiating laser light on the reflecting mirror.

5. A charged particle beam apparatus comprising the stage apparatus according to claim 1.

6. A stage apparatus comprising:
a base;
a sample stage that is capable of being moved to the base;
a reflecting mirror that is provided on the sample stage;
a laser interferometer that measures a position of the sample stage by irradiating laser light on the reflecting mirror;
a control device that controls a position of the sample stage;
an absolute position detection device that measures an absolute amount of a distance between the base and the sample stage; and
a third position detection device that is different from the laser interferometer and the absolute position detection device and that measures a position along the same axis as the laser interferometer and the absolute position detection device, wherein
the control device positions the sample stage in a position that the laser interferometer and the absolute position detection device are capable of detecting and changes an Abbe error offset amount of the laser interferometer by position information measured by the absolute position detection device.

7. The stage apparatus according to claim 6, wherein the sample stage is configured so as to be moved up to a position in which the laser light is not irradiated on the reflecting mirror, and
when the sample stage is positioned in a position in which the laser light is not irradiated on the reflecting mirror, the control device controls a position of the sample stage by the third position detection device.

8. The stage apparatus according to claim 7, wherein the third position detection device is configured so as to detect a position in an entire movable range of the sample stage.

9. The stage apparatus according to claim 6, wherein the absolute position detection device is arranged so that a measuring direction thereof is generally matched with an optical axis of the laser light.

10. The stage apparatus according to claim 9, wherein the absolute position detection device is arranged on a plane different from that of the reflecting mirror on the sample stage.

11. The stage apparatus according to claim 6, wherein when the sample stage is moved, the control device determines whether to perform a change in the offset amount.

12. The stage apparatus according to claim 11, wherein when coordinates of the sample stage before movement are out of a measurement range of the laser interferometer, and target coordinates after the movement are within the measurement range of the laser interferometer and irradiation of charged particle beams is performed after the movement, the control device performs a change in the offset amount.

13. The stage apparatus according to claim 11, wherein when an elapsed time is stored after a change in the offset amount is performed, the sample stage is within the measurement range of the laser interferometer, and the elapsed time is more than a threshold, the control device performs a change in the offset amount.

14. The stage apparatus according to claim 11, wherein the control device includes a thermometer that measures a temperature of the sample stage, and
when the sample stage is within the measurement range of the laser interferometer and a temperature of the sample stage is more than the threshold, the control device performs a change in the offset amount.

15. The stage apparatus according to claim 6, wherein in the absolute position detection device, an absolute-value output-type linear scale is used.

16. The stage apparatus according to claim 6, wherein in the absolute position detection device, an electrostatic capacity displacement meter is used.

17. The stage apparatus according to claim 6, wherein in the absolute position detection device, image information obtained by an optical microscope is used.

18. The stage apparatus according to claim 6, wherein in the absolute position detection device, image information obtained by charged particle beams is used.

19. A charged particle beam apparatus comprising the stage apparatus according to claim 6.

20. A stage apparatus comprising:
a base;
a sample stage that is capable of being moved to the base;
a reflecting mirror that is provided on the sample stage;
a laser interferometer that measures a position of the sample stage by irradiating laser light on the reflecting mirror;
a control device that controls a position of the sample stage;
a second position detection means that is different from the laser interferometer that specifies a position of the sample stage; and
an absolute position restriction means that restricts an absolute amount of a distance between the base and the sample stage, wherein
the control device controls the sample stage so that the sample stage is restricted by a position of the laser interferometer and the absolute position restriction means and changes an Abbe error offset amount of the laser interferometer by position information of the second position detection means in a state in which the sample stage is restricted by the absolute position restriction means wherein the sample stage is configured so as to be moved out of the stage movement range that the first position detection device is capable of detecting, and the control device adjusts the offset amount after the sample stage is moved out of the stage movement range that the first position detection device is capable of detecting.

21. The stage apparatus according to claim 20, wherein the sample stage includes a pressing member, the base includes a pressed member, and the absolute position restriction device performs restriction by pressing the pressing member against the pressed member.

22. A charged particle beam apparatus comprising the stage apparatus according to claim 20.

* * * * *